United States Patent
Speer et al.

(10) Patent No.: US 8,852,513 B1
(45) Date of Patent: Oct. 7, 2014

(54) SYSTEMS AND METHODS FOR PACKAGING INTEGRATED CIRCUIT GAS SENSOR SYSTEMS

(75) Inventors: Raymond Speer, Dalkey (IE); Leon Cavanagh, Loughrea (IE); Peter Smith, Summertown (GB); John Pavelka, Austin, TX (US)

(73) Assignee: Silicon Laboratories Inc., Austin, TX (US)

( * ) Notice: Subject to any disclaimer, the term of this patent is extended or adjusted under 35 U.S.C. 154(b) by 519 days.

(21) Appl. No.: 13/250,810

(22) Filed: Sep. 30, 2011

(51) Int. Cl.
*G01N 27/403* (2006.01)
*G01N 27/407* (2006.01)

(52) U.S. Cl.
USPC .......................................... 422/83; 204/424

(58) Field of Classification Search
CPC .......... G01N 27/4062; G01N 27/4065; G01N 27/4078; G01N 27/129; G01N 27/27
See application file for complete search history.

(56) References Cited

U.S. PATENT DOCUMENTS

| | | |
|---|---|---|
| 4,057,823 A | 11/1977 | Burkhardt et al. |
| 4,580,439 A | 4/1986 | Manaka |
| 4,638,346 A | 1/1987 | Inami et al. |
| 4,649,364 A | 3/1987 | Tanahashi et al. |
| 4,793,181 A | 12/1988 | Djorup |
| 4,831,381 A | 5/1989 | Hester |
| 4,849,798 A | 7/1989 | Wantanabe |
| 4,876,890 A | 10/1989 | Mercer et al. |
| 4,931,851 A | 6/1990 | Sibbald et al. |
| 5,279,855 A | 1/1994 | Hafele et al. |
| 5,296,125 A | 3/1994 | Glass et al. |
| 5,357,149 A | 10/1994 | Kimura |
| 5,481,129 A | 1/1996 | DeJong et al. |
| 5,605,612 A | 2/1997 | Park et al. |
| 5,801,428 A | 9/1998 | Felde et al. |
| 5,814,281 A | 9/1998 | Williams et al. |
| 5,878,332 A | 3/1999 | Wang et al. |
| 5,942,372 A | 8/1999 | West et al. |
| 6,017,775 A | 1/2000 | Igel et al. |
| 6,051,854 A | 4/2000 | Vigna et al. |
| 6,111,280 A | 8/2000 | Gardner et al. |
| 6,407,449 B1 | 6/2002 | Takikawa et al. |
| 6,417,026 B2 | 7/2002 | Gotoh et al. |
| 6,537,347 B2 * | 3/2003 | Motouji et al. ..................... 95/8 |
| 6,647,782 B2 | 11/2003 | Toyoda |

(Continued)

FOREIGN PATENT DOCUMENTS

| | | |
|---|---|---|
| JP | 358111747 | 7/1983 |
| JP | 63103957 | 10/1986 |

(Continued)

OTHER PUBLICATIONS

JPO computer-generated English language translation of Aranishi et al. JP 2012-78089 A, patent published Apr. 19, 2012.*

(Continued)

*Primary Examiner* — Alex Noguerola
(74) *Attorney, Agent, or Firm* — Egan, Peterman & Enders LLP.

(57) ABSTRACT

Systems and methods are provided for packaging integrated circuit (IC) gas sensor systems that employ at least one gas sensor that is formed as part of an integrated circuit and configured to sense the presence and/or concentration of a target gas or other gas characteristics that may be present in the ambient gaseous environment surrounding the packaged IC gas sensor system.

21 Claims, 4 Drawing Sheets

(56) References Cited

U.S. PATENT DOCUMENTS

| | | |
|---|---|---|
| 6,673,644 B2 | 1/2004 | Gole et al. |
| 6,690,569 B1 | 2/2004 | Mayer et al. |
| 6,724,612 B2 | 4/2004 | Davis et al. |
| 6,774,613 B1 | 8/2004 | Becker et al. |
| 7,554,134 B2 | 6/2009 | Cummins |
| 7,622,080 B2 | 11/2009 | Enquist |
| 7,709,828 B2 | 5/2010 | Braithwaite et al. |
| RE41,889 E | 10/2010 | Ferrari et al. |
| 7,888,708 B2 | 2/2011 | Yazawa et al. |
| 7,980,116 B2 | 7/2011 | Koda et al. |
| 8,007,167 B2 | 8/2011 | Cummins |
| 2002/0141136 A1 | 10/2002 | Toyoda et al. |
| 2003/0010119 A1 | 1/2003 | Toyoda |
| 2003/0010988 A1 | 1/2003 | Franson |
| 2004/0008471 A1 | 1/2004 | Davis et al. |
| 2005/0097941 A1 | 5/2005 | Sandvik et al. |
| 2005/0188764 A1 | 9/2005 | Itakura et al. |
| 2005/0199975 A1 | 9/2005 | Matubara |
| 2008/0061323 A1 | 3/2008 | Yazawa et al. |
| 2009/0141767 A1 | 6/2009 | Cummins |
| 2009/0273009 A1 | 11/2009 | Cummins |
| 2009/0308747 A1 | 12/2009 | Cramer et al. |
| 2009/0324449 A1 | 12/2009 | Kira |
| 2010/0098593 A1 | 4/2010 | Trakhtenberg et al. |
| 2011/0089439 A1 | 4/2011 | Cummins |
| 2011/0089472 A1 | 4/2011 | Cummins |
| 2011/0098937 A1 | 4/2011 | Cummins |
| 2011/0186995 A1 | 8/2011 | Alvarado et al. |
| 2011/0197657 A1 | 8/2011 | Gole |
| 2011/0198732 A1 | 8/2011 | Lin et al. |
| 2011/0210446 A1 | 9/2011 | Liao et al. |
| 2011/0226041 A1 | 9/2011 | Cummins |
| 2012/0032692 A1* | 2/2012 | Kothari et al. ........... 324/672 |
| 2012/0113650 A1 | 5/2012 | Inoue |

FOREIGN PATENT DOCUMENTS

| | | | |
|---|---|---|---|
| JP | 404361149 | 12/1992 | |
| JP | 2012-78089 A | * 4/2012 | ............ G01N 27/12 |
| WO | WO2006/090433 A1 | 8/2006 | |
| WO | WO2007/097025 A1 | 8/2007 | |
| WO | WO2007/099933 A1 | 9/2007 | |

OTHER PUBLICATIONS

Speer et al., "Gas Sensor Having Integral Heater", U.S. Appl. No. 13/250,456, filed Sep. 30, 2011, 26 pgs.

Speer et al., "Gas Sensor Utilizing Integrated Circuit Redistribution Layer", U.S. Appl. No. 13/250,432, filed Sep. 30, 2011, 26 pgs.

Speer et al., "Integrated Gas Sensor", U.S. Appl. No. 13/250,414, filed Sep. 30, 2011, 26 pgs.

Smith et al., "Methods and Materials for Forming Gas Sensor Structures", U.S. Appl. No. 13/250,831, filed Sep. 30, 2011, 27 pgs.

Smith et al., "Gas Sensor Materials and Methods for Preparation Thereof", U.S. Appl. No. 13/250,849, filed Sep. 30, 2011, 27 pgs.

Fis, "Fis Gas Sensor, SB-500-12, for Carbon Monoxide Detection", Mar. 2006, 2 pgs.

Lemme, Elektronik, "CMOS-Sensoren gehort die Zukunft", vol. 43, No. 24, Nov. 1994, 10 pgs.

Bousse et al., "A Process for the Combined Fabrication of Ion Sensors and CMOS Circuits", IEEE Electron Device Letters, vol. 9, No. 1, Jan. 1988, 3 pgs.

Baltes et al., "Micromachined Thermally Based CMOS Microsensors", Proceedings of the IEEE, vol. 86, No. 8, Aug. 1998, 19 pgs.

Baltes et al., "The Electronic Nose in Lilliput", Proceedings of the IEEE, vol. 35, No. 9, Sep. 1998, 4 pgs.

McCartney et al., "A Fully Integrated Sensor Interface Chip", Solid State Circuits Conference Esscirc, 1999, 4 pgs.

Cratlon, "C701 802.15.4 Zigbee Ready Wireless Sensor Module", 2004. 1 pg.

Morris et al., "Pt(II) As an Electronically Active Surface Site in the Room Temperature CO Response of Pt Modified Gas Sensitive Resistors", J. Physc. Chem. B, 2001, 8 pgs.

Aqili et al., "Effect of Antimony Doping on the Structure, Electrical and Optical Properties of Tin Oxide Thin Films", Sci. Int., 18(1), 2006, 3 pgs.

* cited by examiner

SYSTEMS AND METHODS FOR PACKAGING INTEGRATED CIRCUIT GAS SENSOR SYSTEMS

RELATED APPLICATIONS

This application is related to the following applications, all concurrently filed on the same date as the present application, including U.S. patent application Ser. No. 13/250,414, entitled "Integrated Gas Sensor"; U.S. patent application Ser. No. 13/250,432, entitled "Gas Sensor Utilizing Integrated Circuit Redistribution Layer"; U.S. patent application Ser. No. 13/250,456, entitled "Gas Sensor Having Integral Heater"; U.S. patent application Ser. No. 13/250,849, entitled "Gas Sensor Materials and Methods for Preparation Thereof"; and U.S. patent application Ser. No. 13/250,831, entitled "Methods and Materials for Forming Gas Sensor Structures" the disclosures of which are all expressly incorporated by reference herein in their entirety.

TECHNICAL FIELD OF THE INVENTION

The disclosure herein relates to gas sensing, and more particularly to packages for integrated circuit (IC) gas sensor systems.

BACKGROUND

A wide variety of gas sensor types are utilized to detect gases and other ambient air conditions. For example, electrochemical sensors are well known. Such sensors may include the use of a metal or plastic can, which houses a liquid electrolyte having electrodes immersed in the liquid. An opening or gas diffusion barrier allows atmosphere to ingress and make contact with a gas-sensing electrode. Infrared sensors are also well known. Infrared sensors advantageously utilize the characteristics of gases which show differing absorption spectrum at various infrared frequencies. Further, metal oxide based gas sensors, such as sensors employing precious metal (Pt, Pd, Au, Ag)-activated $SnO_2$, are also known. Such sensors may utilize porous metal oxides which exhibit a shift in electrical parameters when exposed to differing gases. For example, such electrical parameters may include resistance and capacitance characteristics. Such metal oxide sensors may be housed in a metal and/or plastic cylindrical can or ceramic housing with an opening provided on one end of the can to allow ingress of gas through an active charcoal filter to contact a porous metal oxide bead that is positioned within the can. Often such metal oxide based sensors utilize high operation temperatures, for example as high as 300 to 500 degrees Celsius.

The use of metal oxide based gas sensor materials in combination with integrated circuit technology to provide an integrated gas sensor has been described in U.S. Pat. No. 7,554,134, issued Jun. 30, 2009 to Cummins, and U.S. Pat. No. 8,007,167, issued Aug. 30, 2011 to Cummins, both of which are assigned to the present assignee and the disclosures of both of which are expressly incorporated by reference herein in their entirety. As described in U.S. Pat. Nos. 7,554,134 and 8,007,167 a single chip wireless gas sensor may include metal oxide sensing materials combined with a microcontroller, wireless transmit/receive circuitry, and other electrical circuits, all on a single integrated circuit.

SUMMARY OF THE INVENTION

Disclosed herein are systems and methods for packaging integrated circuit (IC) gas sensor systems which employ at least one gas sensor that is formed as part of an integrated circuit and configured to sense the presence and/or concentration of a target gas (e.g., such as carbon monoxide and/or methane) or other gas characteristics (e.g., such as humidity) that may be present in the ambient gaseous environment surrounding the packaged IC gas sensor system. In one embodiment, the disclosed systems and methods may be implemented with a IC package that includes a sensor housing having a sensor cavity defined therein for operably containing an IC gas sensor system disposed therein, and in a further exemplary embodiment, the IC package for the IC gas sensor system may be advantageously configured to be compatible with standard IC packaging techniques. In one embodiment, the IC gas sensor system may include an integrated circuit (e.g., containing a processor and memory) that has one or more gas sensor structures (e.g., electrodes, heating elements, etc.) formed thereon that are configured to sense a target gas concentration and other gas characteristics using one or more gas sensitive regions.

In addition to providing electrical contacts within the sensor cavity for purposes of interconnecting the IC gas sensor system to external circuitry, the sensor cavity of the IC package may also be configured to provide a contained gas sensing environment within which the gas sensor of the IC gas sensor system may be operated for gas sensing purposes. In this regard, the sensor housing may be provided with at least one gas entry opening therein that is contiguous with the sensor cavity for allowing entry of gas into the sensor cavity where the gas may contact one or more sensor elements (e.g., gas sensing electrodes) of the gas sensor. Electrical contacts may be provided within the sensor cavity that are configured for electrical interconnection with bonding pads of the IC gas sensor system, e.g., such as through bond wires or solder bumps. Corresponding electrical contacts (e.g., solder bumps, bonding pads, etc.) may in turn be provided on the exterior of the sensor housing that are electrically coupled to the electrical contacts provided within the sensor cavity. This configuration allows integrated circuitry of the IC gas sensor system to be interconnected to external circuitry outside the housing of the gas sensor package (i.e., via the coupled interior and exterior electrical contacts of the gas sensor package) for purposes of receiving electrical power and interchanging electrical signals with the external circuitry. Examples of such external circuitry include, but are not limited to, circuitry contained on a printed circuit board (PCB) or the like.

In one exemplary embodiment, one or more selected filter materials (e.g., such as activated carbon in the form of activated carbon cloth or a permeable cartridge of powdered activated carbon) may be optionally provided in a gas entry path between the gas entry opening in the sensor housing and the sensor cavity defined within the housing. Such filter material/s may be provided for purposes of filtering out contaminants other than the target gas present in the ambient gas that may interfere with accurate gas sensing measurements by the gas sensor and/or that may adversely affect components of the IC gas sensor system. Optional appropriate sensor component/s (e.g., such as electrodes) may be present to monitor the status of the filter material/s. For example, electrical resistance of an activated carbon filter material may drop as the filter material becomes saturated with trapped contaminants that are removed from the ambient gas that enters the sensor cavity through the filter material. Accordingly, spaced-apart electrodes may be provided to monitor the resistance of the filter materials so that appropriate action (e.g., alarm or sensor shut-down) may be taken when a predetermined drop in electrical resistance across the filter material indicates that the amount of contaminant saturation in the filter material has reached an undesired level and/or indicates onset of filter saturation. In one exemplary embodiment, a microcontroller component of the gas sensor system may be configured to monitor the status (e.g., resistance) of the filter material, and to take the appropriate action upon detection of undesired contaminant saturation level.

In one respect, disclosed herein is 1. A packaged integrated circuit gas sensor system, including: an integrated circuit package having a sensor cavity and a separate filter cavity defined therein; an integrated circuit gas sensor system disposed within the sensor cavity; and at least one filter material disposed within the filter cavity. The filter cavity may be in fluid communication with an ambient gaseous atmosphere outside the package, and the filter cavity may be in fluid communication with the sensor cavity to form a gas entry path through the filter material between the outside ambient gaseous atmosphere and the sensor cavity defined within the package. The sensor cavity is sealed from the outside ambient gaseous atmosphere except for the gas entry path through the filter material.

In another respect, disclosed herein is a method for packaging an integrated gas sensor system, the method including: providing an integrated circuit package having a sensor cavity and a separate filter cavity defined therein; disposing an integrated circuit gas sensor system within the sensor cavity; disposing at least one filter material within the filter cavity; and sealing the integrated circuit from an ambient gaseous atmosphere outside the package except for a gas entry path through the filter material. The filter cavity of the so formed package may be in fluid communication with the ambient gaseous atmosphere outside the package, and the filter cavity may be in fluid communication with the sensor cavity to form the gas entry path through the filter material between the outside ambient gaseous atmosphere and the sensor cavity defined within the package.

In another respect, disclosed herein is a method for sensing at least one target gas, including providing a packaged integrated circuit gas sensor system that includes an integrated circuit package having a sensor cavity and a separate filter cavity defined therein, the filter cavity being in fluid communication with an ambient gaseous atmosphere outside the package, the sensor cavity being sealed from the outside ambient gaseous atmosphere except for a gas entry path through the filter cavity, an integrated circuit gas sensor system disposed within the sensor cavity, and at least one filter material disposed within the filter cavity. The method may further include allowing gas from the outside ambient gaseous atmosphere to enter the sensor cavity via the gas entry path through the filter material disposed in the filter cavity to filter out one or more contaminants other than the target gas from the entered gas; and using the integrated circuit gas sensor system to sense one or more characteristics of the target gas that enters the sensor cavity via the gas entry path through the filter material.

DETAILED DESCRIPTION OF THE INVENTION

Figure 1:
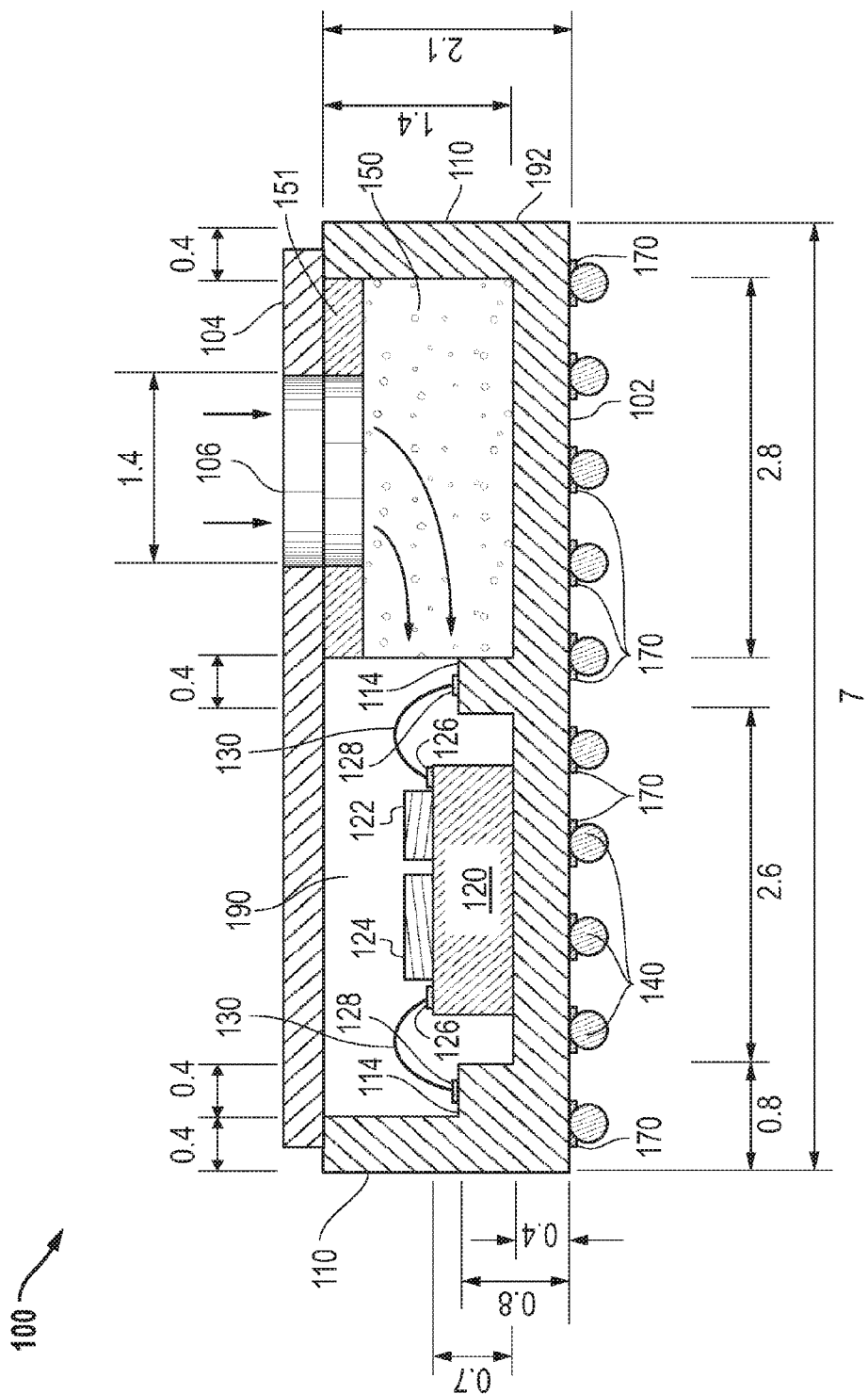
FIG. 1 illustrates a cross-sectional side view of a packaged integrated circuit (IC) gas sensor system according to one exemplary embodiment of the disclosed systems and methods.

FIG. 1 illustrates a cross-sectional side view of an exemplary embodiment of a packaged integrated circuit (IC) gas sensor system 100 that includes a sensor housing 102 and a lid 104 that is coupled in sealing relationship to the sensor housing 102 so as to define a sensor cavity 190 within the packaged system 100. As shown, sensor cavity 190 contains an integrated circuit 120 (e.g., containing at least one processing device and memory) that has multiple gas sensor structures 122 and 124 formed thereon that are configured to sense parameters such as a target gas concentration and other gas characteristics using one or more gas sensitive regions. In one exemplary embodiment described further herein, integrated circuit 120 of FIG. 1 may be configured for gas sensing analysis by virtue of the presence of a microcontroller, memory (e.g., including non-volatile memory), analog to digital converter, digital to analog converter, temperature sensor, humidity sensor and gas sensor all on a single integrated circuit 120 within package 100. The microcontroller and memory may provide lookup tables, correlation tables, mathematical algorithms and the like for processing all the collected data together in order to provide a more accurate gas concentration reading. In operation, data collected by the various on chip sensors may be converted from analog levels to digital with the analog to digital converter. The digital data may then be provided to the microcontroller to perform calculations to determine a gas concentration from the sensed measurements. The microcontroller may then provide a digital output at an output pin of the integrated circuit 120 to provide the detected concentration to a user.

As further shown in FIG. 1, an optional and separate filter cavity 192 is defined within the packaged system 100 adjacent to and in fluid communication with sensor cavity 190, and filter material 150 is disposed within filter cavity 192 to filter out, absorb or otherwise reduce or remove contaminant constituents/gases that would otherwise interfere with the performance of the gas sensor system 100. A gas entry opening 106 (e.g., via, port, etc.) is defined in lid 104 as shown to allow ambient gas from outside the packaged IC gas sensor system 100 to enter the sensor cavity 190 through the filter material disposed in the filter cavity 150 in a similar path as shown by the arrows, and in a manner in which substantially all of the gas entering the sensor cavity 190 must pass through the filter material 150. A filter seal 151 (e.g., an epoxy ring or other suitable sealing structure) is provided as shown between lid 104 and filter material 150, and is positioned to contact and form a gaseous seal between lid 104 and filter material 150 so that ambient gas (e.g., ambient air) entering opening 106 must travel through filter material 150 of filter cavity 192 prior to entering filter cavity 192. In this regard, lid 104 may be affixed to housing 102 in any manner (e.g., using ultrasonic welding, soldering, etc.) that is suitable for forming a hermetic seal between lid 104 and housing 102 such that opening 106 forms the only gas entry path into sensor cavity 190. As shown in this embodiment, sensor structures 122 and 124 and integrated circuit 190 are exposed to the environment within sensor cavity 190.

Figure 2:
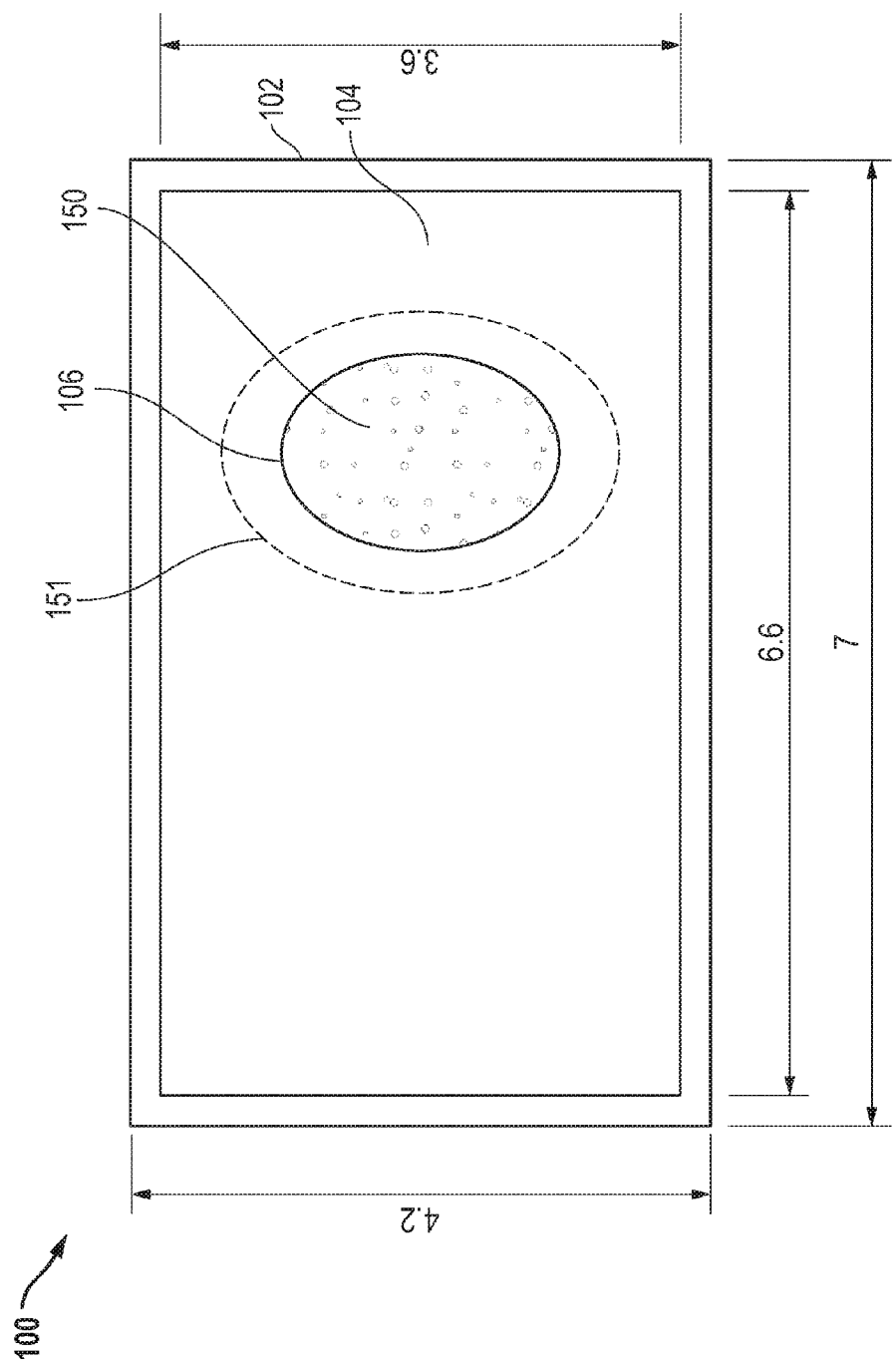
FIG. 2 illustrates an overhead view of a packaged integrated circuit (IC) gas sensor system according to one exemplary embodiment of the disclosed systems and methods.

FIG. 2 illustrates an overhead view of packaged IC gas sensor system 100 with the epoxy ring of filter seal 151 of FIG. 1 shown in dashed outline beneath lid 104 and in position relative to gas entry opening 106. FIGS. 1 and 2 illustrate exemplary dimensions in millimeters for components of a packaged IC gas sensor system 100 of FIGS. 1-4. It will be understood that these dimensions are exemplary only, and that any other suitable dimension may be employed.

Still referring to FIG. 1, integrated circuit 120 may be any type of electronic circuitry suitable for utilization with one or more sensor elements for detecting characteristics of gas compositions that enter sensor cavity 190. In one exemplary embodiment, integrated circuit 120 may be a mixed signal system on a chip circuit that includes a processor such as an 8051 compatible microcontroller in combination with associated memory elements as described in more detail in concurrently filed U.S. patent application Ser. No. 13/250,414, entitled "Integrated Gas Sensor", the disclosure of which is expressly incorporated herein by reference in its entirety.

Sensor structures such as structures 122 and 124 of FIG. 1 may be any suitable structures that are configured to sense a target gas concentration and/or other gas characteristics using one or more gas sensitive regions. Examples of possible sensor structures that may be present alone or in various combinations on an IC 120 within sensor cavity 190 include, but are not limited to, planar-interdigitated or parallel-plate resistance/capacitance gas/humidity sensors.

In one exemplary embodiment, sensor structure 122 may be a planar gas sensor structure for sensing a constituent gas concentration (e.g., such as carbon monoxide and/or methane) that has two electrodes separated by a gas sensitive metal oxide material, e.g. a tin oxide ($SnO_2$) doped with platinum and antimony such as disclosed in concurrently filed U.S. patent application Ser. No. 13/250,849, entitled "Gas Sensor Materials and Methods for Preparation Thereof", and in concurrently filed U.S. patent application Ser. No. 13/250,831, entitled "Methods and Materials for Forming Gas Sensor Structures" the disclosure of each of which is expressly incorporated by reference in its entirety. Such a gas sensitive material exhibits a variation in electrical resistance as the amount of gas that the gas sensitive material is exposed to varies. In such a embodiment, planar interdigitated fingers of two separate conductive elements may form one gas sensing electrode while the other gas sensing electrode may be formed by a third conductive element winding between the interdigitated fingers of first two conductive elements. Applications for a packaged IC gas sensor system 100 configured for carbon monoxide detection include, but are not limited to, household or industrial carbon monoxide detectors that detect unhealthy levels of carbon monoxide in closed buildings, fire detectors that sense fire by detecting low levels of carbon monoxide, etc.

In a further exemplary embodiment, sensor structure 124 may be a planar capacitive humidity sensor positioned in close proximity to a carbon monoxide sensor structure 122, such that sensor structure 124 may be utilized to measure humidity within sensor cavity 190 for purposes of calibrating the carbon monoxide sensor structure 122 to correct for the environmental influence of humidity on sensed carbon monoxide concentration. The humidity sensor may utilize a variety of humidity sensing techniques and may be formed in a variety of manners. In one exemplary approach, sensor structure 124 may utilize two interdigitated conductors formed in a semiconductor redistribution layer (RDL) conductor layer with an overlaying humidity sensitive dielectric layer, such as a polybenzoxazole (PBO) or polyimide layer or other suitable dielectric layer, that extends down between the two conductors and over the two conductors. The capacitance between the two conductors may change as moisture ingresses into the dielectric layer, and capacitance variations may be utilized to reflect variations in the relative humidity. As so configured in this embodiment, sensor structure 124 is positioned downstream in the gas travel path from filter material 150 so that sensor structure 124 is exposed to the same environmental characteristics (e.g., environmental humidity) that affects sensor structure 122. Capacitive humidity sensing techniques may include, for example, the techniques described in U.S. Pat. No. 8,007,167 to Cummins, the disclosure of which is incorporated herein by reference in its entirety.

Further information on the aforementioned sensor embodiments may be found described in more detail in said concurrently filed U.S. patent application Ser. No. 13/250,414, entitled "Integrated Gas Sensor", the disclosure of which is expressly incorporated herein by reference in its entirety. It will be understood that any one or more alternative types of sensor structures may be similarly positioned and coupled to an integrated circuit 120 of a packaged integrated circuit (IC) gas sensor system 100 for detecting concentrations of other types of gases and/or for detecting characteristics of a gas other than humidity. In this regard, other embodiments may include, for example, multiple gas sensors with specific materials and configuration selective to particular gases or airborne artifacts.

In the exemplary embodiment of FIG. 1, an integrated circuit 120 may include bond pads 126 that are provided to allow external connections to corresponding peripherally spaced interior bond pads 128 of sensor housing 102 via wire bonds 130 as shown. In this embodiment, bond pads 128 are provided on raised internal contact surfaces 114 that are peripherally spaced around the sides of sensor cavity 190 of sensor housing 102 in position for interconnection with IC bond pads 126 via wire bonds 130. However, it will be understood that an integrated circuit 120 may be alternatively provided with any other configuration, geometry and type of bond pads, solder bumps, leads or other contact and/or interconnect structures for connection to correspondingly configured interior bond pads or other corresponding contact structures of a sensor housing 102, e.g., such as using flip chip solder bumps placed on integrated circuit 120 in a grid array configuration that mates with a corresponding array of interior housing bond pads provided on the bottom interior surface of housing cavity 190.

As shown in FIG. 1, sensor housing 102 may in turn be configured with exterior bond pads 170 that are electrically coupled through the housing external walls 110 to the interior bond pads 128. In the illustrated embodiment, exterior bond pads 128 are located on the bottom surface of sensor housing 102 and are configured for coupling to external circuitry (e.g., such as a PCB or other circuitry) via ball grid array (BGA) solder balls 140 that are configured in a ball grid array (BGA) pattern. However, it will be understood that FIG. 1 is exemplary only, and that any other suitable package interconnection structures and technology may be employed for electrically coupling a packaged integrated circuit (IC) gas sensor system 100 to external circuitry including, but not limited to, peripheral gull wing leads, wire bonds, pins or pin grid array (PGA), etc. Moreover, exterior contact structures, such as bond pads, may be provided on any other exterior surface/s of sensor housing 102 and/or in any other geometrical configuration that is suitable for electrically coupling a packaged integrated circuit (IC) gas sensor system 100 to external circuitry.

Figure 3:
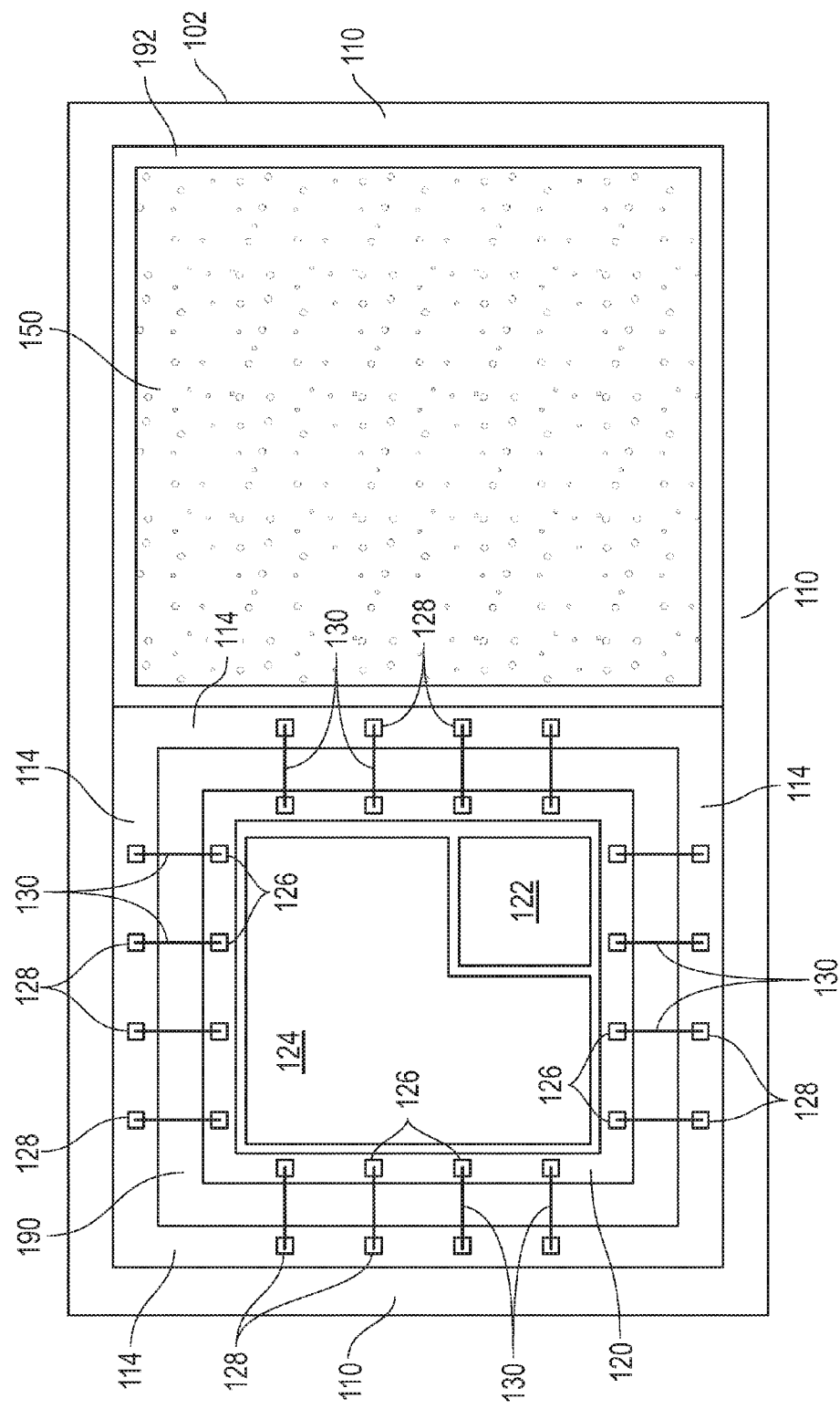
FIG. 3 illustrates an overhead view of components of a packaged integrated circuit (IC) gas sensor system according to one exemplary embodiment of the disclosed systems and methods.

FIG. 3 illustrates an overhead view of one exemplary embodiment of packaged IC gas sensor system 100 of FIGS.

1 and 2 with lid 104 removed. Visible in FIG. 3 are top surface of filter material 150 contained within filter cavity 192. Also visible are top surface of integrated circuit 120 disposed in sensor cavity 190 with regions of sensor structures 122 and 124 formed thereon. In FIG. 3, wire bonds 130 are shown connecting bond pads 126 of integrated circuit 120 with corresponding bond pads 128 of sensor housing 102. It will be understood that the number and configuration of bond wires 130, and bond pads 126 and 128 is exemplary only. For example, in one exemplary embodiment packaged IC gas sensor system 100 may be configured as a 10 pin package, having 5 bond pads 126 disposed adjacent each of two opposing sides of IC 120 and having 7 bond pads 126 disposed adjacent each of the two remaining opposing sides of IC 120.

It will be understood that the materials and construction of housing 102 and lid 104 of packaged IC gas sensor system 100 may be according to any suitable semiconductor package configuration. Fabrication of housing 102 for a packaged IC gas sensor system 100 may be, for example, in accordance with standard semiconductor packaging techniques and examples of suitable semiconductor packaging types that may be employed include, but are not limited to, ceramic packages, plastic packages, and combinations thereof.

In the practice of the disclosed systems and methods, any suitable type of gas permeable filter material or combination of such filter material/s 150 may be employed to fit the characteristics of a given ambient gas composition to be sensed and/or characteristics of gas sensor structure/s employed inside sensor cavity 190. For example, in the exemplary embodiment where a carbon monoxide sensor structure 122 is employed, a filter material may be activated carbon in the form of activated carbon cloth, a gas permeable cartridge of powdered activated carbon or carbon foam. Other examples of suitable filter materials include, but are not limited to, hydrophobic membranes.

It will be understood that the particular above-described configuration of housing 102 and lid 104 of FIG. 1 is exemplary only, and that other configurations may be employed. For example, positioning of one or more gas entry openings is not limited to lid 104, but rather may be in any position suitable for allowing ambient gas to enter sensor cavity 190, e.g., a gas entry opening may be positioned on a side or bottom wall of housing 102 with or without an intervening filter material provided in a gas entry path therebetween. Further, it will be understood that a gas entry opening 106 need not be positioned to one side of sensor cavity 190 as shown, but rather may be alternately positioned directly over sensor cavity 190 (e.g., with or without an intervening filter material provided in a gas entry path therebetween). Moreover, shape and size of a gas entry opening/s 106 may vary as appropriate to fit the needs or desires for a particular gas sensing application. Thus, for example, a gas entry opening may be provided in a lid 104 and/or in one or more walls of a housing 102 as a circular opening, square opening, irregular-shaped opening, as an array of multiple openings, etc. In one exemplary embodiment, size of gas entry opening 106 may be an elliptical shape having a length of about 2.25 mm and width of about 1.4 mm, although this is merely an example and it will be understood that a wide variety of other shapes and/or sizes may be employed. In one embodiment, a gas entry opening may be suitably tailored in size in order to regulate the amount of analyte interacting with the downstream sensors, although this is not necessary in other embodiments where the amount of analyte interacting with the downstream sensors does not matter.

Figure 4:
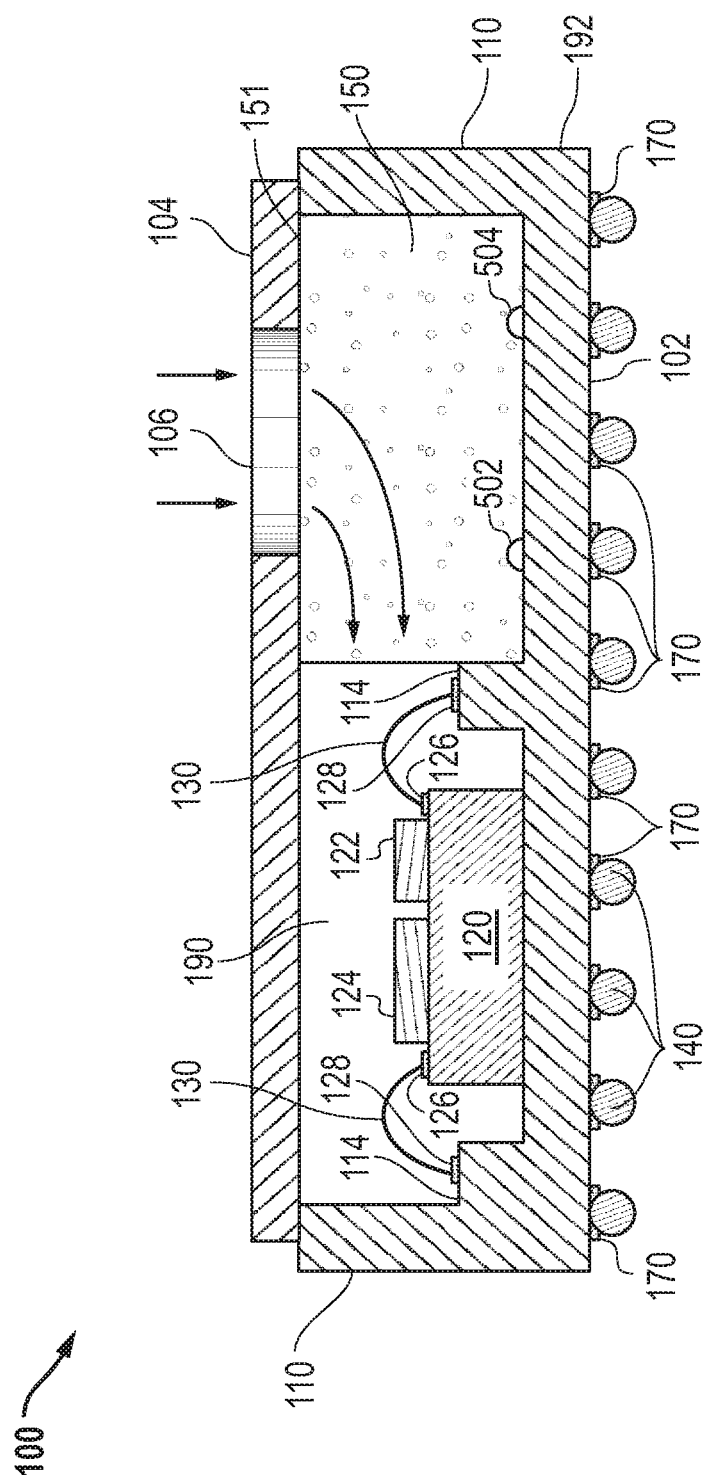
FIG. 4 illustrates a cross-sectional side view of a packaged integrated circuit (IC) gas sensor system according to one exemplary embodiment of the disclosed systems and methods.

It will be understood that the presence of filter seal 151 of FIGS. 1 and 2 is optional, and that a packaged IC gas sensor system 100 may be provided with a filter material 150 using any other alternative configuration that is suitable for maintaining a filter material 150 in position for filtering gas entering sensor cavity 190. For example, FIG. 4 illustrates an alternative embodiment of a packaged IC gas sensor system 100 in which a filter material 150 is held in position between lid 104 and the interior surface/s of housing 102 without the presence of filter seal 151. In one such embodiment, the filter material 150 (e.g., such as activated carbon cloth) may be positioned within housing 102 as shown (or otherwise between lid 104 and housing 102), and then lid 104 affixed to housing 102 in a hermetically sealed manner (e.g., using ultrasonic welding, soldering, etc.) and in a manner that compresses and holds the filter material against the interior of filter housing 102 with opening 106 positioned immediately above filter material 150, e.g., without otherwise affixing the filter material 150 to either the lid 104 or housing 102. In another embodiment, a filter material 150 may be first affixed (e.g., using suitable adhesive) to the underside of lid 104 adjacent opening 106, and then lid 104 aligned with housing 102 such that the filter material 150 is placed into filter cavity 192 when lid 104 is in turn affixed to housing 102.

In a further embodiment, an insert component (e.g., one or more metal insert/s) may be optionally placed inside filter cavity 192 together with filter material 150 so as to suitably adjust the interior size 192 of filter cavity 192 so that the cavity 192 may easily accommodate filter materials and filter material components of differing sizes, e.g., filter material components having different thicknesses may be accommodated including those filter material components having thicknesses less than the depth of the interior of cavity 192. For example, in one exemplary embodiment, such a metal insert may be positioned between lid 104 and the top of filter material 150, e.g., in a position and configuration similar to that of optional filter seal 151 of FIG. 1. In an alternative example, such a metal insert may be positioned beneath filter material 150 between filter material 150 and the interior bottom surface of sensor housing 102, e.g., so as to compress and hold an undersized filter material against the lid 104 with lid gas entry opening 106 positioned immediately above filter material 150. It will also be understood that when placed between a lid gas entry opening 106 and the filter material 150 (in similar position to filter seal 151), such an optional metal insert may be provided with a corresponding opening of a specific size (e.g., reduced cross-sectional area relative to opening 106) so as to allow/regulate the ingression of gas to the sensing regions downstream. In another embodiment, opening size within optional filter seal 151 of FIG. 1 may be similarly configured for the same purpose (e.g., to have a cross-sectional gas entry area that is less than the cross sectional gas entry opening of gas entry opening 106).

In a further embodiment, electrical resistance of a filter material 150 (e.g., activated carbon) may be optionally monitored over time to detect the presence of contaminant build up in the filter material. In this regard, the measured resistance across a given segment of the filter material 150 tends to drop as the filter material 150 absorbs contaminant gas molecules (e.g., such as isopropyl alcohol vapours) that are removed from the ambient gas that enters the sensor cavity 190 through the filter material 150, and as the filter material 150 becomes saturated with these trapped contaminants. A saturated filter material 150 offers no protection against contaminant gas exposure and can make a gas sensor system liable to false positive alarms.

Accordingly, as further shown in the exemplary embodiment of FIG. 4, spaced-apart electrodes 502 and 504 may be provided to extend (e.g., as conductive bumps) from a bottom interior surface of filter cavity portion 192 of housing 102 as shown to make electrical contact with filter material 150, it being understood that two or more of such spaced apart electrodes may be positioned in any other alternative location and/or configured in other manner suitable for measuring resistance of filter material 150 between the electrodes. Electrodes 502 and 504 may in turn be electrically coupled (e.g., via wire bonds 130 or other suitable interconnect structures) to resistance measurement circuitry that may be present in integrated circuit 120. Alternatively, electrodes 502 and 504 may be electrically coupled via solder balls 140 or other suitable interconnect structures to resistance measurement circuitry that is external to package 100. In any case, controller circuitry or other suitable processing device internal or external to package 100 may be configured to monitor the resistance of the filter material 150 and to take appropriate action (e.g., to provide an alarm or sensor shut-down signal) when electrical resistance across the filter material 150 drops below a predetermined threshold resistance value (e.g., indicating that the amount of contaminant saturation in the filter material 150 has exceed reached an undesired level). Such a predetermined threshold resistance value may be stored, for example, in memory of integrated circuit 120.

In another exemplary embodiment, a microcontroller within integrated circuit 120 may be configured to apply correction factors based on measured filter material electrical resistance to the detected gas concentration values from gas sensor structure 122 and/or to output a signal to a user that is representative of the amount of filter material contamination (or remaining filter material life or capacity) based on electrical resistance correlation factors. Such correction and/or correlation factors may be maintained, for example, in a lookup table within memory of integrated circuit 120.

Further modifications and alternative embodiments of this invention will be apparent to those skilled in the art in view of this description. It will be recognized, therefore, that the present invention is not limited by these example arrangements. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the implementations and architectures. For example, equivalent elements may be substituted for those illustrated and described herein and certain features of the invention may be utilized independently of the use of other features, all as would be apparent to one skilled in the art after having the benefit of this description of the invention.

The invention claimed is:

1. A packaged integrated circuit gas sensor system, comprising:
   an integrated circuit package having a sensor cavity and a separate filter cavity defined therein;
   an integrated circuit gas sensor system disposed within the sensor cavity; and
   at least one filter material disposed within the filter cavity;
   where the filter cavity is in fluid communication with an ambient gaseous atmosphere outside the package, and the filter cavity is in fluid communication with the sensor cavity to form a gas entry path through the filter material between the outside ambient gaseous atmosphere and the sensor cavity defined within the package;
   where the sensor cavity is sealed from the outside ambient gaseous atmosphere except for the gas entry path through the filter material; and
   where the integrated circuit package further comprises:
   a sensor housing,
   a package lid coupled in sealing relationship to the sensor housing to form the sensor cavity and the separate filter cavity within the package, and
   a gas entry opening defined in the package lid in fluid communication with the filter cavity, the filter cavity being in fluid communication with the ambient gaseous atmosphere through the gas entry opening.

2. The system of claim 1, where the integrated circuit comprises at least one processing device and memory electrically coupled thereto.

3. The system of claim 1, where the integrated circuit gas sensor system comprises a gas sensor structure formed thereon that is configured to detect at least one of carbon monoxide, methane, or a combination thereof.

4. The system of claim 1, where the filter material comprises activated carbon cloth.

5. The system of claim 1, where the package further comprises one or more interior contact structures disposed in an interior of the package that are electrically coupled through the package to one or more exterior contact structures disposed on the exterior of the package; where the integrated circuit comprises one or more contact structures electrically coupled to the interior contact structures of the package; and where the exterior contact structures are configured to be electrically coupled to circuitry that is external to the package to provide electrical signal communication between the integrated circuit and the external circuitry.

6. The system of claim 1, further comprising at least two spaced-apart electrodes in electrical contact with the filter material in the filter cavity.

7. The system of claim 6, where the spaced-apart electrodes are coupled to resistance measurement circuitry in the integrated circuit, the resistance measurement circuitry being configured to monitor the resistance of the filter material across the spaced-apart electrodes and to take at least one action when the measured electrical resistance across the filter material drops below a predetermined threshold resistance value.

8. The system of claim 1, where the integrated circuit gas sensor system comprises an integrated circuit with at least one gas sensor structure formed thereon, the gas sensor structure comprising at least one gas sensitive region for sensing one or more characteristics of gas that enters the sensor cavity via the gas entry path through the filter material, and the gas sensor structure being electrically coupled to provide one or more signals to the integrated circuit representative of the one or more measured characteristics of the entered gas; and where the integrated circuit is configured for processing the signals received from the gas sensor structure.

9. The system of claim 1, where the integrated circuit gas sensor system comprises a temperature sensor, humidity sensor and gas sensor structure formed thereon.

10. A packaged integrated circuit gas sensor system, comprising:
    an integrated circuit package having a sensor cavity and a separate filter cavity defined therein;
    an integrated circuit gas sensor system disposed within the sensor cavity; and
    at least one filter material disposed within the filter cavity;
    where the filter cavity is in fluid communication with an ambient gaseous atmosphere outside the package, and the filter cavity is in fluid communication with the sensor cavity to form a gas entry path through the filter material between the outside ambient gaseous atmosphere and the sensor cavity defined within the package;

where the sensor cavity is sealed from the outside ambient gaseous atmosphere except for the gas entry path through the filter material; and where the integrated circuit gas sensor system comprises an integrated circuit with at least one gas sensor structure formed thereon, the gas sensor structure comprising at least one gas sensitive region for sensing one or more characteristics of gas that enters the sensor cavity via the gas entry path through the filter material, and the gas sensor structure being electrically coupled to provide one or more signals to the integrated circuit representative of the one or more measured characteristics of the entered gas; and where the integrated circuit is configured for processing the signals received from the gas sensor structure.

11. A packaged integrated circuit gas sensor system, comprising:

an integrated circuit package having a sensor cavity and a separate filter cavity defined therein;

an integrated circuit gas sensor system disposed within the sensor cavity; and at least one filter material disposed within the filter cavity;

where the filter cavity is in fluid communication with an ambient gaseous atmosphere outside the package, and the filter cavity is in fluid communication with the sensor cavity to form a gas entry path through the filter material between the outside ambient gaseous atmosphere and the sensor cavity defined within the package;

where the sensor cavity is sealed from the outside ambient gaseous atmosphere except for the gas entry path through the filter material; and where the integrated circuit gas sensor system comprises a temperature sensor, humidity sensor and gas sensor structure formed thereon.

12. A method for packaging an integrated gas sensor system, the method comprising:

providing an integrated circuit package having a sensor cavity and a separate filter cavity defined therein;

disposing an integrated circuit gas sensor system within the sensor cavity;

disposing at least one filter material within the filter cavity; and sealing the integrated circuit from an ambient gaseous atmosphere outside the package except for a gas entry path through the filter material, the filter cavity being in fluid communication with the ambient gaseous atmosphere outside the package, and the filter cavity being in fluid communication with the sensor cavity to form the gas entry path through the filter material between the outside ambient gaseous atmosphere and the sensor cavity defined within the package;

where the integrated circuit package comprises a sensor housing and a package lid, a gas entry opening being defined in the package lid; and where the method further comprises:

coupling the package lid to the sensor housing in sealing relationship to form the sensor cavity with the integrated circuit contained therein and the filter cavity with the filter material contained therein such that the filter cavity is in fluid communication with the ambient gaseous atmosphere through the gas entry opening.

13. The method of claim 12, where the integrated circuit comprises at least one processing device and memory electrically coupled thereto.

14. The method of claim 12, where the filter material comprises activated carbon cloth.

15. The system of claim 12, where the package further comprises one or more interior contact structures disposed in an interior of the package that are electrically coupled through the package to one or more exterior contact structures disposed on the exterior of the package, the exterior contact structures being configured to be electrically coupled to circuitry that is external to the package to provide electrical signal communication between the integrated circuit and the external circuitry; and where the method further comprises electrically coupling one or more contact structures of the integrated circuit to the interior contact structures of the package.

16. The method of claim 12, further comprising providing at least two spaced-apart electrodes in electrical contact with the filter material in the filter cavity; and electrically coupling the spaced-apart electrodes to resistance measurement circuitry in the integrated circuit, the resistance measurement circuitry being configured to monitor the resistance of the filter material across the spaced-apart electrodes and to take at least one action when the measured electrical resistance across the filter material drops below a predetermined threshold resistance value.

17. A method for sensing at least one target gas, comprising:

providing a packaged integrated circuit gas sensor system comprising:

an integrated circuit package having a sensor cavity and a separate filter cavity defined therein, the filter cavity being in fluid communication with an ambient gaseous atmosphere outside the package, and the sensor cavity being sealed from the outside ambient gaseous atmosphere except for a gas entry path through the filter cavity, an integrated circuit gas sensor system disposed within the sensor cavity, and at least one filter material disposed within the filter cavity;

allowing gas from the outside ambient gaseous atmosphere to enter the sensor cavity via the gas entry path through the filter material disposed in the filter cavity to filter out one or more contaminants other than the target gas from the entered gas; and using the integrated circuit gas sensor system to sense one or more characteristics of the target gas that enters the sensor cavity via the gas entry path through the filter material;

where the integrated circuit package further comprises:

a sensor housing, a package lid coupled in sealing relationship to the sensor housing to form the sensor cavity and the separate filter cavity within the package, and a gas entry opening defined in the package lid in fluid communication with the filter cavity, the filter cavity being in fluid communication with the ambient gaseous atmosphere through the gas entry opening to form the gas entry path into the sensor cavity, and where the method further comprises allowing the gas from the outside ambient gaseous atmosphere to enter the gas entry path of the package through the gas entry opening defined in the package lid.

18. A method for sensing at least one target gas, comprising:

providing a packaged integrated circuit gas sensor system comprising:

an integrated circuit package having a sensor cavity and a separate filter cavity defined therein, the filter cavity being in fluid communication with an ambient gaseous atmosphere outside the package, and the sensor cavity being sealed from the outside ambient gaseous atmosphere except for a gas entry path through the filter cavity,
- an integrated circuit gas sensor system disposed within the sensor cavity, and
- at least one filter material disposed within the filter cavity;

allowing gas from the outside ambient gaseous atmosphere to enter the sensor cavity via the gas entry path through the filter material disposed in the filter cavity to filter out one or more contaminants other than the target gas from the entered gas; and using the integrated circuit gas sensor system to sense one or more characteristics of the target gas that enters the sensor cavity via the gas entry path through the filter material;

where the integrated circuit gas sensor system comprises an integrated circuit with at least one gas sensor structure with at least one gas sensitive region formed thereon; and where the method further comprises:
- using the gas sensor structure to sense one or more characteristics of the gas that enters the sensor cavity via the gas entry path through the filter material, and providing one or more signals to the integrated circuit representative of the one or more measured characteristics of the entered gas, and
- using the integrated circuit to process the signals received from the gas sensor structure.

19. The method of claim 18, further comprising providing signals from the integrated circuit to circuitry that is external to the package, the signals based on the sensed characteristics of the target gas that enters the sensor cavity.

20. The method of claim 18, further comprising monitoring the electrical resistance of the filter material; and taking at least one action when the measured electrical resistance across the filter material drops below a predetermined threshold resistance value.

21. The method of claim 18, where the integrated circuit package further comprises:
- a sensor housing;
- a package lid coupled in sealing relationship to the sensor housing to form the sensor cavity and the separate filter cavity within the package; and
- a gas entry opening defined in the package lid in fluid communication with the filter cavity, the filter cavity being in fluid communication with the ambient gaseous atmosphere through the gas entry opening to form the gas entry path into the sensor cavity; and where the method further comprises allowing the gas from the outside ambient gaseous atmosphere to enter the gas entry path of the package through the gas entry opening defined in the package lid.

* * * * *